United States Patent [19]

Barner et al.

[11] Patent Number: 4,582,919
[45] Date of Patent: Apr. 15, 1986

[54] PROCESS FOR THE MANUFACTURE OF OPTICALLY ACTIVE COMPOUNDS

[75] Inventors: Richard Barner, Witterswil; Josef Hübscher, Seon, both of Switzerland

[73] Assignee: Hoffmann-La Roche Inc., Nutley, N.J.

[21] Appl. No.: 619,654

[22] Filed: Jun. 11, 1984

[30] Foreign Application Priority Data

Jun. 21, 1983 [CH] Switzerland .................. 3391/83

[51] Int. Cl.$^4$ .................. C07D 303/12; C07C 41/00; C07C 43/02
[52] U.S. Cl. .................. 549/554; 549/415; 568/651
[58] Field of Search .................. 549/554, 415; 568/651

[56] References Cited

U.S. PATENT DOCUMENTS 3,992,420 11/1976 Lind et al. .................. 549/554

OTHER PUBLICATIONS

Katsuki et al., Journ. Am. Chem. Soc. 102, 5974 (1980).
Normant, Synthesis, p. 63, (1972)
Corey et al., Journ. Am. Chem. Soc. 94 (20), 7210 (1972).
Chem. Abstracts 98:215447k (1983).
Chem. Abstracts 98:143279g (1983).

*Primary Examiner*—Ethel G. Love
*Attorney, Agent, or Firm*—Jon S. Saxe; George M. Gould; John J. Maitner

[57] ABSTRACT

There is described a novel process for producing hydroquinone derivatives of the formula

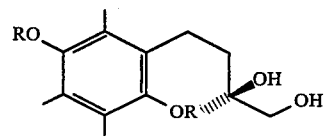

II wherein R is an ether protecting group, and their conversion into d-α-tocopherol, starting from compounds of the formula

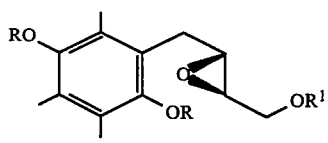

I wherein R is an ether protecting group and R$^1$ is hydrogen or an ether protecting group.

8 Claims, No Drawings

PROCESS FOR THE MANUFACTURE OF OPTICALLY ACTIVE COMPOUNDS

BACKGROUND OF THE INVENTION

This invention relates to a novel process for manufacturing hydroquinone derivatives as intermediates in manufacturing d-α-tocopherol (natural vitamin E). The invention also relates to the novel starting materials and intermediates in this process.

Several of the known processes for manufacturing natural vitamin E are of limited interest to industry. Natural vitamin E has been prepared through extraction from natural sources. Since the tocopherol content of these natural sources is small, large amounts of the natural source must be processed to yield amounts of the natural tocopherol. Additionally the processes are cumbersome.

There exists a need for an industrial process for producing natural vitamin E in good yield and with high optical purity. The present invention provides such a process.

SUMMARY OF THE INVENTION

In accordance with this invention, a new synthesis is provided, including novel intermediates thereto, comprising reducing a compound of the formula

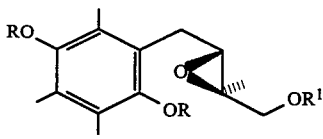

I wherein R is an ether protecting group and R¹ is hydrogen or an ether protecting group,
with hydrogen in the presence of Raney-nickel or, where R¹ represents an ether protecting group, with lithium aluminium hydride, converting the reduction product of the formula

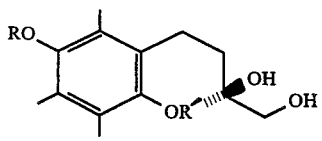

II wherein R is as above,
into an epoxide, reacting the epoxide of the formula

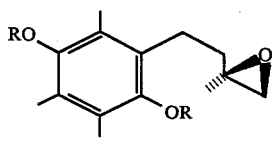

III wherein R is as above,
with a Grignard compound of the formula

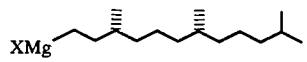

IV wherein X represents bromine or chlorine, and, converting the product of the Grignard reaction of the formula

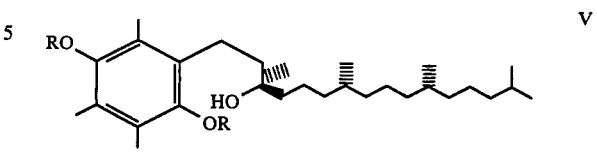

V wherein R is as above,
into d-α-tocopherol of the formula

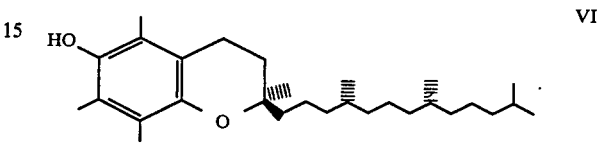

VI

DETAILED DESCRIPTION OF THE INVENTION

The term "ether protecting group" designates any ether which upon hydrolysis or oxidation yields the hydroxy group. Any conventional ether that can be hydrolyzed or oxidized to yield the acid can be utilized as the protecting group. In the case of hydrolysis suitable ether protecting groups are silyl, alkoxymethyl or tetrahydropyranyl. The term "alkoxy" as used herein is taken to mean a lower alkoxy group containing 1 to 6 carbon atoms such as methoxy, ethoxy, propoxy, isopropoxy, etc. An example of an alkoxymethyl group is methoxymethyl. In the case of oxidation suitable ether protecting groups are any ether protecting groups which upon oxidation yield the hydroxy group. Suitable ether protecting groups are for example the alkyl ethers. The term "alkyl" means a saturated aliphatic straight chain hydrocarbon containing from 1 to 6 carbon atoms such as ethyl, methyl, isopropyl, etc.

In the pictorial representation of the compounds given throughout this application, a tapered "━▬" notation indicates a substituent that is situated above the plane of the molecule, while the tapered " ⅲⅲ" multiple line notation indicates a substituent situated below the plane of the molecule.

In accordance with this invention, a compound of formula I is converted to a compound of formula II which is then converted to a compound of formula III which is then converted by the reaction steps described below to the d-α-tocopherol.

The reduction of a compound of formula I with hydrogen in the presence of Raney-nickel can be carried out when R¹ is hydrogen or an ether protecting group. The reduction is conveniently carried out in an aqueous system. In carrying out this reaction any water-miscible organic solvent can be used. Exemplary water miscible organic solvents are lower alcohols, ethers or ketones. Exemplary lower alcohols are methanol, ethanol, propanol, etc. Exemplary ethers are tetrahydrofuran and dioxan. An exemplary ketone is acetone. Furthermore, the reduction can be carried out in a neutral to slightly alkaline range, especially in a pH-range of about 7-10, and at a temperature in the range of room temperature to about 100° C. The preferred temperature range is from about 70° C. to about 100° C. More particularly it is preferred that the reaction be carried out at the reflux temperature of the reaction mixture. An especially preferred embodiment of this reaction uses a solvent mixture having a boiling point as close as possible to 100° C.

In another embodiment when $R^1$ is an ether protecting group, the reduction reaction can be carried out using lithium aluminum hydride (LiAlH$_4$). This reduction can be carried out under conditions typical for reductions with LiAlH$_4$. Exemplary of those conditions utilize ether as solvent and running the reaction at room temperature.

The conversion of a compound of formula II into an epoxide of formula III can be carried out in a conventional manner known to one skilled in the art. For this purpose, the primary hydroxy group in formula II is converted, as is well known in the art, into a leaving group. The term "leaving group" designates any conventional leaving group especially groups such as, for example, halides (especially chloride, bromide or iodide), sulfonic acid esters (especially tosylate or mesylate) and the like. The compound containing said leaving group is subsequently treated with a base. Suitable bases include inorganic and organic bases. Preferred bases are inorganic bases. Especially preferred bases are sodium hydroxide or potassium hydroxide and the like.

The reaction of an epoxide of formula III with a Grignard compound of formula IV can be carried out in a conventional manner well known in the art. A preferred embodiment for this reaction is the use of copper (I or II) catalysts. Especially preferred catalyst is copper (I) n-propylacetylide or a copper (I) halide-dimethyl sulfide complex. In carrying out this reaction any solvent usually used in Grignard reactions may be used.

The compounds of formula V are known and can be converted into d-α-tocopherol as known in the art. In one embodiment, where the R group is cleaved by hydrolysis, then the conversion can be carried out by treatment with acid. In another embodiment where the R group is cleaved by oxidation, then the conversion can be carried out as is well known by treatment with, for example, ceric ammonium nitrate [(Ce(NH$_4$)$_2$-(NO$_3$)$_6$] and subsequent reductive cyclization of the quinone obtained.

The starting materials, compounds of the formula I, used in accordance with the invention are novel. However, compounds of formula I can be prepared in a manner well known in the art according to the following Scheme. In formulae VII and IX, R is as above and X is chlorine or bromine.

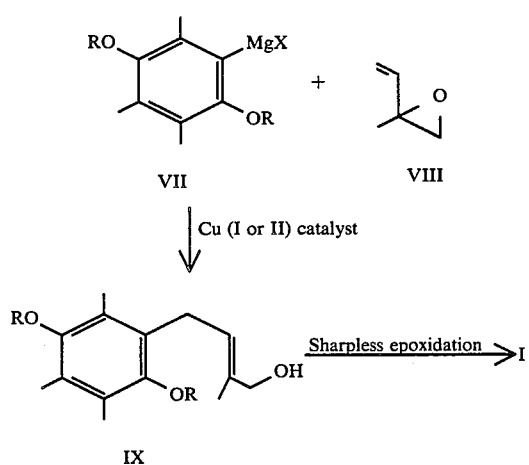

The reaction of a compound VII with the isoprene oxide VIII can be carried out under conditions usual for a Grignard reaction, in the presence of a copper (I or II) catalyst. A preferred copper catalyst is lithium tetrachlorocuprate. The subsequent Sharpless epoxidation is a reaction well known in the art and can be carried out under the usual conditions.

The compounds VII and VIII are well known and can be prepared by methods well known in the art. The compound IX are novel and are an object of the present invention.

The following examples illustrate the present invention.

EXAMPLE 1

185 mg of (2R,3R)-4-(2',5'-dimethoxy-3',4',6'-trimethylphenyl)-2,3-epoxy-2-methylbutanol were dissolved in 5 ml of methanol and the solution was subsequently diluted with 5 ml of water. Thereupon, Raney-nickel was added and the mixture was heated at reflux for 2 hours under hydrogen. After completion of the hydrogen uptake, the mixture was filtered, washed with methanol and methylene chloride and concentrated on a rotary evaporator. Residual water was distilled off azeotropically by the addition of methylene chloride. The oil obtained was recrystallized from hexane/ether and there were obtained 161 mg of 55% (S)-4-(2',5'-dimethoxy-3',4',6'-trimethylphenyl)-2-methyl-1,2-butanediol (48% yield; analysis of the acetonide by gas chromatography). Data of the pure substance: m.p. 86°–87° C. $[\alpha]_D^{20}$ +2.55° (c=5.3% in CHCl$_3$).

The (2R,3R)-4-(2',5'-dimethoxy-3',4',6'-trimethylphenyl)-2,3-epoxy-2-methylbutanol used as the starting material can be prepared as follows:

(a) 26.7 mmol of 2,5-dimethoxy-3,4,6-trimethylbenzylmagnesium bromide were treated at −78° C. with 3.6 g of lithium tetrachlorocuprate (Li$_2$CuCl$_4$) as a 0.1 molar solution in tetrahydrofuran. 2.2 g (26 mmol) of isoprene oxide were subsequently added. The mixture was thereupon stirred at −78° C. for 1 hour and at room temperature for 3–4 hours. 10 ml of saturated ammonium chloride were then added at 0° C. and the mixture was extracted with ether. After drying the ether extract over sodium sulphate, concentration and crystallization from ethyl ether at −20° C., there were obtained 4.7 g (75%) of 4-(2',5'-dimethoxy-3',4',6'-trimethylphenyl)-2-methyl-2-butenol with a melting point of 85°–86° C.

(b) 0.594 ml of titanium tetraisopropoxide was dissolved in 10 ml of dry methylene chloride. Thereupon, 524 mg of dibutyl D-tartrate were added dropwise at −20° C. and the mixture was left to stand at −20° C. for 10 minutes. 197 mg of 4-(2',5'-dimethoxy-3',4',6'-trimethylphenyl)-2-methyl-2-butenol were then added and subsequently a further 180 mg of tert.butyl hydroperoxide (80%) were added dropwise (as a solution in 0.5 ml of methylene chloride). The thus-obtained yellow solution was left to stand at −20° C. for 4 to 5 days, then treated with 5 ml of 1N sodium hydroxide solution, left to warm to room temperature and stirred for 1 hour. The phases were then separated, the aqueous phase was washed twice with methylene chloride, the organic phases were dried over sodium sulphate and concentrated. The colourless oil obtained was dissolved in 20 ml of ethyl ether and stirred with 5 ml of 1N sodium hydroxide solution for 1 hour. The phases were again separated, the aqueous phase was washed twice with ethyl ether, the organic phases were dried over sodium sulphate and concentrated. There were obtained 188 mg (98%) of (2R,3R)-4-(2',5'-dimethoxy-3',4',6'-trimethylphenyl)-2,3-epoxy-2-methylbutanol. $[\alpha]_D^{20}$ +18.2° (c=2% in chloroform).

EXAMPLE 2

1.10 g of (2R,3R)-4-(2',5'-dimethoxy-3',4',6'-trimethylphenyl)-2,3-epoxy-2-methylbutanol were dissolved in 2 ml of pyridine. 0.5 ml of trimethylchlorosilane was then added and the mixture was left to stand at room temperature for 1 hour. Sodium bicarbonate solution was thereupon added and the mixture was extracted with toluene. The organic phases were dried over sodium sulphate and concentrated. The thus-obtained (2R,3R)-4-(2',5'-dimethoxy-3',4',6'-trimethylphenyl)-2,3-epoxy-2-methyl-1-(trimethylsilyloxy)-butane was dissolved in 10 ml of ether, treated with 40 mg of lithium aluminium hydride and stirred at room temperature for 16 hours. Ammonium hydrogen difluoride solution was then added and the mixture was subsequently extracted with ethyl acetate. The organic phases were dried over sodium sulphate, concentrated and dried further in a high vacuum. There were thus obtained 804 mg (73%) of (S)-4-(2',5'-dimethoxy-3',4',6'-trimethylphenyl)-2-methyl-1,2-butanediol.

M.p. 86°-87° C. $[\alpha]_D^{20}$ +2.53° (c=5.3% in CHCl$_3$).

The (2R,3R)-4-(2',5'-dimethoxy-3',4',6'-trimethylphenyl)-2,3-epoxy-2-methylbutanol used as the starting material can be prepared in a manner analogous to that described in Example 1.

EXAMPLE 3

237 mg of tosyl chloride and 350 mg of (S)-4-(2',5'-dimethoxy-3',4',6'-trimethylphenyl)-2-methyl-1,2-butanediol were dissolved in 1 ml of methylene chloride. 0.180 ml of pyridine was then added dropwise at 0° C. and the mixture was left to stand at 0° C. for 1 hour and then at room temperature for 16 hours. 1 g of ice and 0.3 ml of concentrated hydrochloric acid were thereupon added. The mixture was then extracted with methylene chloride and the extracts were dried and concentrated. There were obtained 511 mg (95%) of (S)-4-(2',5'-dimethoxy-3',4',6'-trimethylphenyl)-2-methyl-1-toluylsulphonyloxy-2-butanol. $[\alpha]_D^{20}$ +1.2° (c=2.6% in chloroform).

177 mg of (S)-4-(2',5'-dimethoxy-3',4',6'-trimethylphenyl)-2-methyl-1-toluylsulphonyloxy-2-butanol were dissolved in 1 ml of ethanol and the solution was treated with 0.3 ml of alcoholic potassium hydroxide solution (1.5N). The mixture was left to stand at room temperature for 10 minutes, 30 ml of methylene chloride were then added and the resulting mixture was dried over sodium sulphate and concentrated. There were obtained 105 mg of (S)-4-(2',5'-dimethoxy-3',4',6'-trimethylphenyl)-2-methyl-1,2-epoxybutane. M.p 47°–48° C. $[\alpha]_D^{20}$ +4.91° (c=2.2% in chloroform).

EXAMPLE 4

5.8 mmol of (3R,7R)-3,7,11-trimethyl-dodecyl bromide were heated at reflux in 20 ml of ethyl ether for 0.25 hour with calcinated magnesium. 1 g of (S)-4-(2',5'-dimethoxy-3',4',6'-trimethylphenyl)-2-methyl-1,2-epoxybutane and 0.9 g of copper (I) 2-propylacetylide [or 1.2 g of copper (I) bromide-dimethyl sulphide complex] were than added at 0° C. The temperature of the mixture was subsequently left to rise to room temperature and the mixture was stirred overnight. 10 ml of ammonium chloride were then added and the mixture was extracted with ethyl ether. The extract was dried, concentrated and distilled in a bulb-tube (b.p.$_{0.01}$=140° C.). There were obtained 1.28 g (72%) [or 1.41 g (79%)] of (3R,7R,11R)-1-(2',5'-dimethoxy-3',4',6'-trimethylphenyl)-3,7,11,15-tetramethylhexadecan-3-ol as a colourless oil. $[\alpha]_D^{20}$ −0.67° (c=0.9% in chloroform).

C$_{31}$H$_{56}$O$_3$ (476.79). Calculated: C=78.09; H=11.84. Found: C=77.92; H=11.88.

EXAMPLE 5

1.38 g of cerium (IV) ammonium nitrate in 5 ml of water were added while stirring to a solution of 530 mg (1.12 mmol) of (3R,7R,11R)-1-(2',5'-dimethoxy-3',4',6'-trimethylphenyl)-3,7,11,15-tetramethylhexadecan-3-ol in 50 ml of acetonitrile and this mixture was stirred at room temperature for 1 hour. The mixture was extracted three times with 20 ml of methylene chloride each time, the combined organic phases were dried over sodium sulphate and evaporated on a rotary evaporator. There were obtained 480 mg of (3'R,7'R,11'R)-2-(3'-hydroxy-3',7',11',15'-tetramethylhexadecan-1'-yl)-3,4,5-trimethyl-1,4-benzoquinone.

The product was dissolved in 100 ml of methanol and hydrogenated over 10% Pd/C. 0.5 ml of concentrated hydrochloric acid was then added and the mixture was heated to 50° C. for 2 hours. Thereafter, the mixture was neutralized by the addition of solid sodium hydrogen carbonate and subsequently filtered. The filtrate was evaporated and the residue was chromatographed on silica gel with toluene/ethyl acetate (2:1). In this manner there were obtained 375 mg (90%) of 2R,4'R,8'R-α-tocopherol (d-α-tocopherol) as a slightly yellowish oil. The enantiomeric purity of the d-α-tocopherol obtained in the above manner gave a value of 95%.

We claim:

1. A process for producing hydroquinone derivatives of the formula

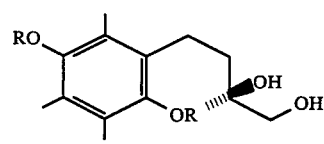

II wherein R is an ether protecting group
by reducing a compound of the formula

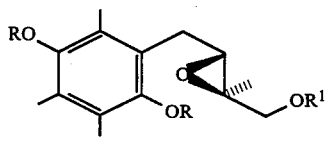

I wherein R is as above and R$^1$ is hydrogen or an ether protecting group,
with hydrogen in the presence of Raney-nickel or, where R$^1$ is an ether protecting group, with lithium aluminium hydride.

2. The process of claim 1, wherein said reduction with Raney-Nickel is carried out in an aqueous medium.

3. The process of claim 2, wherein the reduction is carried out at a pH of from about 7 to about 10.

4. The process of claim 3, wherein the reduction is carried out at a temperature of about 70° C. to about 100° C.

5. A compound of the formula
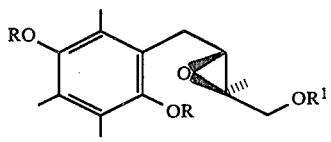
wherein R is an ether protecting group and $R^1$ is hydrogen or an ether protecting group.
6. The compound of claim 5, wherein R is alkyl, silyl, alkoxymethyl or tetrahydropyranyl.
7. The compound of claim 6, wherein $R_1$ is hydrogen.
8. The compound of claim 7 which is (2R,3R)-4-(2',5'-dimethoxy-3',4',6'-trimethylphenyl)-2,3-epoxy-2-methylbutanol.
* * * * *